US006564088B1

(12) United States Patent
Soller et al.

(10) Patent No.: US 6,564,088 B1
(45) Date of Patent: May 13, 2003

(54) PROBE FOR LOCALIZED TISSUE SPECTROSCOPY

(75) Inventors: Babs R. Soller, Northboro, MA (US); Tania Khan, Worcester, MA (US)

(73) Assignee: University of Massachusetts, Worcester, MA (US)

( * ) Notice: Subject to any disclaimer, the term of this patent is extended or adjusted under 35 U.S.C. 154(b) by 53 days.

(21) Appl. No.: 09/766,990

(22) Filed: Jan. 22, 2001

Related U.S. Application Data

(60) Provisional application No. 60/177,492, filed on Jan. 21, 2000.

(51) Int. Cl.[7] .............................................. G01N 21/00
(52) U.S. Cl. ...................................................... 600/478
(58) Field of Search ................................. 600/478, 477

(56) References Cited

U.S. PATENT DOCUMENTS

| | | | | |
|---|---|---|---|---|
| 5,441,054 A | * | 8/1995 | Tsuchiya | 600/477 |
| 5,694,931 A | * | 12/1997 | Tsuchiya | 600/477 |
| 5,779,631 A | | 7/1998 | Chance | |
| 5,813,403 A | | 9/1998 | Soller et al. | |
| 6,201,989 B1 | * | 3/2001 | Whitehead et al. | 600/477 |
| 6,377,841 B1 | * | 4/2002 | Lin et al. | 600/478 |
| 6,377,842 B1 | * | 4/2002 | Pogue et al. | 600/478 |
| 6,381,018 B1 | * | 4/2002 | Bigio et al. | 600/478 |

OTHER PUBLICATIONS

David M. Haaland et al. "New Classical Least–Squares/Partial Least–Squares Hybrid Algorithm for Spectral Analyses" (*Applied Spectroscopy*) vol. 55, No. 2, pp. 1–8, 2001.

David M. Haaland et al. "New Prediction–Augmented Classical Least–Squares (PACLS) Methods: Application to Unmodeled Interferents" (*Applied Spectroscopy*) vol. 54, No. 9, pp. 1303–1312, 2000.

David M. Haaland "Synthetic Multivariate Models to Accommodate Unmodeled Interfering Spectral Components during Quantitative Spectral Analyses" (*Applied Spectroscopy*) vol. 54, No. 2, pp. 246–254, 2000.

G. Kumar et al. "Optimal prope geometry for near–infrared spectroscopy of biological tissue " (*Applied Optics*) vol. 36, No. 10, pp. 2286–2293, Apr. 1, 1997.

Tania Khan, Abstract: "NIRS Measurement of Tissue pH: Optimizing Small, Fiber Optic Probe Designs with the Aid of Monte Carlo Simulations" Conference Title: "Biomedical Diagnostic, Guidance, and Surgical–Assist Systems" (BIOS 2000).

Judith R. Mourant et al. "Measuring absorption coefficients in small volumes of highly scattering media: source–detector separations for which path lengths do not depend on scattering properties" (*Applied Optics*) vol. 36, No. 22 pp. 5655–5661 Aug. 1, 1997.

* cited by examiner

*Primary Examiner*—Paul J. Hirsch
(74) *Attorney, Agent, or Firm*—Nutter McClennen & Fish LLP

(57) ABSTRACT

An optical probe structure for illuminating and collecting returned light from a region of tissue. The optical probe is configured with illumination and collection windows to controllably collect light from the region of tissue in vivo. The probe is designed to have a defined spacing between the fiber or fibers connected to the light source, and the fiber or fibers connected to the optical detector, so that light reaching the detector has passed through a localized region of tissue of a small and well-defined size or dimension. The probe can assay or detect tissue cell distribution, a tissue constituent such as hydrogen ions (pH), lactate, or an endogenous tissue component such as hemoglobin, myoglobin, or lipids in plaque. Measurements may indicate conditions such as metabolic state, stress, shock or ischemia in different tissues.

24 Claims, 7 Drawing Sheets

PROBE FOR LOCALIZED TISSUE SPECTROSCOPY

REFERENCE TO RELATED APPLICATION

This application is related to and claims the benefit under 35 U.S.C. 119(e) of U.S. Provisional Patent Application No. 60/177,492, filed by applicants on Jan. 21, 2000.

FIELD OF THE INVENTION

The invention relates to a probe for spectroscopic measurement of tissue.

BACKGROUND OF THE INVENTION

Optical spectroscopy is a valuable tool for determining the chemical composition and concentration of specific analytes present in biological material. In vivo applications of optical spectroscopy to tissue include determining tissue pH, distinguishing cancerous from noncancerous tissue, and analyzing atherosclerotic plaque. Often, such a spectroscopic assay proceeds by measurement of a secondary parameter, e.g., an indicator compound for the condition of interest. The signal analysis may also proceed by relatively complex processing, such as correlation of spectral samples with an empirically-compiled database of tissue spectra. Much of the prior work in this area is accomplished by broad illumination of the sample and collection of reflected, transmitted or emitted light from a large area of the sample.

By way of example, detection of tissue pH by spectroscopic means has been found to be feasible, and to serve as a reliable indicator of tissue damage. Basically, under conditions of greatly reduced blood flow, hydrogen ions accumulate as anaerobic, metabolism commences, resulting in a tissue pH decline, indicating that the tissue is compromised. Irreversible ischemic damage may occur if tissue pH declines to 6.3 pH units or below. Continuous monitoring of tissue pH with suitably constructed electrodes has been known to provide valuable information to the surgeon to assess tissue viability during procedures such as heart surgery, and to monitor post-operative metabolism and blood flow. Spectroscopic monitoring as described for example in U.S. Pat. No. 5,813,403 offers a valuable alternative to such electrode-based monitoring. That patent, which is hereby incorporated herein by reference, describes a method and device for optical measurement of tissue pH. The method employs multivariate calibration techniques to relate reflected light to a reference pH measurement. For open surgery or endosurgical applications, near infrared spectroscopic measurement of tissue pH with such an instrument is useful in identifying regional areas of ischemia. This information can be used to evaluate myocardial protection and to monitor graft patency during or following heart surgery, and may be used to evaluate reperfusion injury during liver transplant procedures.

However a problem inherent in all in vivo tissue spectroscopy applications is that living tissue contains a great number of chemical compounds and physical bodies, and many uncontrolled processes of light absorption and scattering may interfere with the intended spectrographic assay.

It would therefore be desirable to provide an improved method and instrument for in vivo tissue spectroscopy.

SUMMARY OF THE INVENTION

This is achieved in accordance with one aspect of the present invention by a method of tissue spectroscopy, and an instrument for effecting such spectroscopy, wherein an illumination source and detector are arranged to provide a controlled light interaction path through tissue. The controlled path defines a limited interrogation volume, and may, for example, be effective to introduce an effective level of transmittance, for carrying out spectral or calorimetric measurements in the tissue with a minimal scattered component, or to provide effective scattering and transmittance components for determining both spectral and structural features of the interrogated tissue volume.

Both the illumination source and the detector are placed in contact with tissue, either directly or through the use of optical fibers, and an interrogation volume is defined by effective light paths that are determined, for a given set of tissue scattering and absorption properties, by the separation of the source and detector. This may be a banana-, sphere- or other shaped region, and has a limited volume that may be as small as about (0.015) cubic millimeters, or depending on the application, may amount to a volume of three, five or more cubic millimeters.

The size of the region may be initially set based upon structural dimensions of a tissue pathology or characteristic that is to be examined, so as to represent, for example, an expected tumor or tissue layer size dimension, maximumun penetration depth or the like, while the source-detector spacing is set to define a desired form of light interaction and interaction volume for the intended tissue measurement. A preferred system operates with illumination covering a broad band, or with plural discrete illumination sources at different wavelenths in a band, in the near infrared NIR region above about 400 nm.

In various embodiments, an instrument in accordance with the present invention has a probe body that positions the source and detector on or in tissue. An endoscopic or endovascular probe may have a body-insertable main fiber-carrying portion, with a side window or end window geometry, and the source-detector spacing may be adapted to spectroscopically determine tissue pH, cell distribution, or a range of colorimetric and other measurements.

Biological tissue is often heterogeneous and for many applications it is important to analyze light which interacts with a specific volume of sample, e.g., less than 3 $mm^3$. Restriction of the light interaction to a small volume may be complicated by the highly scattering nature of tissue. In some applications it is important to isolate light that has interacted with a specific analyte and to minimize the component of detected light that has been scattered from cellular bodies; yet in other applications the scattered light contains biologically relevant information for the intended assay. A probe of the present invention is tailored to collect light from a specific volume of tissue. It can be fabricated to minimize or enhance the ability to collect scattered light, to collect light from a restricted volume such that the collected signal faithfully reflects an absorbance that is to be measured, or to otherwise enhance sensitivity to a feature of interest.

By collecting light from a very small region of tissue, the present device may enhance accuracy of the method described in U.S. Pat. No. 5,813,403. Specific source detector spacings, shape and positioning for the probe designs of the present invention may be selected based upon Monte Carlo modeling of light propagation through the tissue of interest and source/detector geometry is set accordingly. Prototype calculations for purely scattering media (Intralipid 10%), and for both absorbing compounds (e.g. hemoglobin) and the scattering media, are used to identify potentially suitable source-detector fiber separations, and different models provide source-detector separations that minimize scattering, and/or provide effective scattering information together with an effective transmission path length for spectrographic detection of specific constituents with appropriate localization of the tissue interaction volume for light entering and exiting the tissue. The probes may identify, or quantify components or constituents in the tissue such as hydrogen ions (pH), lactate, or an endogenous tissue component such as hemoglobin, myoglobin, lipids in plaque or the like.

Unless otherwise defined, all technical and scientific terms used herein have the same meaning commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein, including software User's Manuals, are incorporated herein by reference in their entirety. In case of conflict, the present application, including definitions, will control. In addition, the materials, methods, and examples are illustrative only and not intended to be limiting.

BRIEF DESCRIPTION OF THE DRAWINGS

These and other features of the invention will be understood from the disclosure and claims herein, taken together with illustrative figures showing representative embodiments of the invention, wherein:

DETAILED DESCRIPTION

Figure 1:
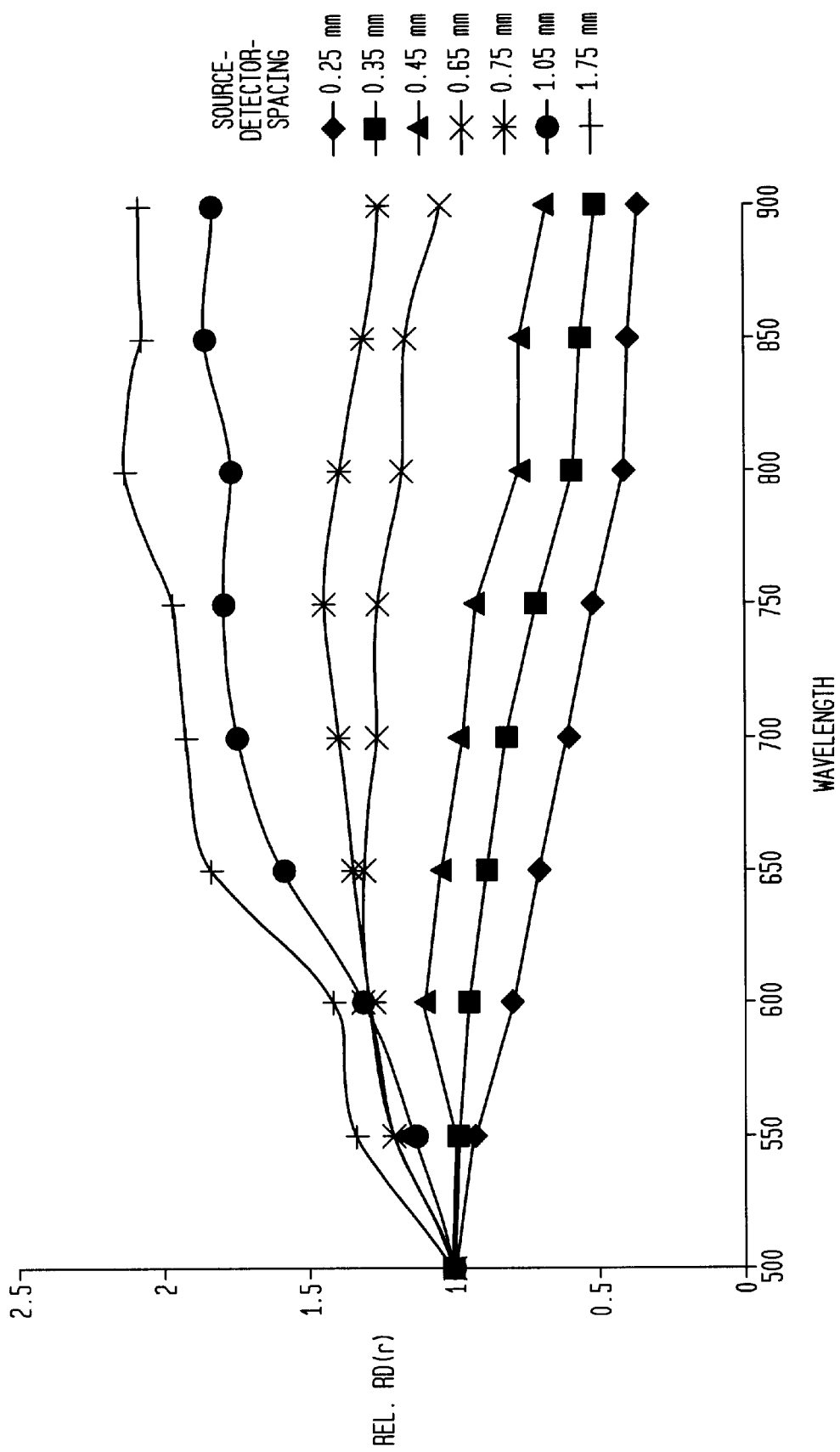
FIG. 1 is a graph of the relative photon output versus wavelength of Monte Carlo simulations for Intralipid.

The present invention addresses the problem of illuminating tissue in vivo and collecting a suitable light signal from the illuminated tissue to perform a spectrographic analysis. Intuitively, the problem may be understood in different implementations, as one of limiting the light present in the collected sample to light that has interacted primarily with the targeted tissue (which may be a thin lamina, or may a tumor or pathological feature of small overall dimension); or to light that has had relevant spectral components absorbed by a targeted analyte over a sufficient path length; or to light that has interacted in a volume selected, in relation to the absorbance characteristics of the tissue and its constituents, such that the detected spectrum optimally represents a targeted material. The probes of the invention may define source-detector light interaction volumes having one or more of the above attributes as well as a scattering interaction. The scattering interaction may provide information about tissue structure, such as cell size, type, presence of edema or the like.

Applicants' invention provides a probe structure that illuminates and collects return light from a tissue bed, that in different embodiments may be cardiac, organ, muscle, vascular or other tissue, and assures that the light-tissue interaction is restricted to a relevant tissue volume and preserves spectral characteristics such that the collected spectrum may be analyzed for tissue features or constituent materials of interest.

This is achieved with an optical probe configured with illumination and collection windows, illustratively with optical fibers, to controllably collect light from a tissue bed in-vivo. The probe is designed to have a determined, and in many embodiments a fixed, spacing between the fiber or fibers connected to the light source, and the fiber or fibers which go to the optical detector, so that light reaching the detector has passed through a localized region of tissue of small and well-defined size or dimension. The specific spacing is application dependent, and may be chosen, for example, based on Monte Carlo modeling of light interaction with the tissue bed to be examined, and an optimization criterion, such as whether or not it is important to detect scattered light. The parameters are set to include scattered light, for example, if the probe is to detect a condition or pathophysiological state in which cell size changes occur. The parameters are also set such that the collected light has traversed an effective path length to include spectrographic information (such as absorbance or transmission information) for one or more materials or analytes of interest in the tissue bed.

Embodiments of the present invention for in-vivo applications such as transcutaneous access or delivery to a tissue site may employ a catheter-like body structure having a body outer diameter less than approximately two millimeters. Other applications, such as instruments for minimally invasive endosurgical use may have somewhat greater dimensions. With such a diameter, probes sized for clinical applications may include two fiber elements or assemblies, one for illumination and one for detection, positioned to interrogate a small region of the myocardium or other tissue. Because of the existing density of cells and their included structures, this geometry allows a realizable source-detector separation on the order of several mean free path lengths for most biological tissues. At this scale, the classical model for a diffusion approximation of photon transport is invalid. Applicant applies Monte Carlo modeling to determine the probe construction for different applications.

Such modeling has been recognized as an appropriate, statistically based model for light transport for a small geometry, and several researchers have identified constructions for stable and effective detection. Illustrative approaches are discussed in Kumar et al., "Optimal probe geometry for near-infrared spectroscopy of biological tissue," Applied Optics 36:2286–2293, 1997, and Mourant et al., "Measuring absorption coefficients in small volumes of highly scattering media: source-detector separations for which path lengths do not depend on scattering properties," Applied Optics 36:5655–5661, 1997. Both of these references are hereby incorporated by reference herein. Monte Carlo simulations of source-detector separations for optimization of other spectroscopy methods and tissue optical property measurements have shown that there exists an optimal separation such that the path length dependence on scattering is minimized for the specified tissue layers.

Figure 2:
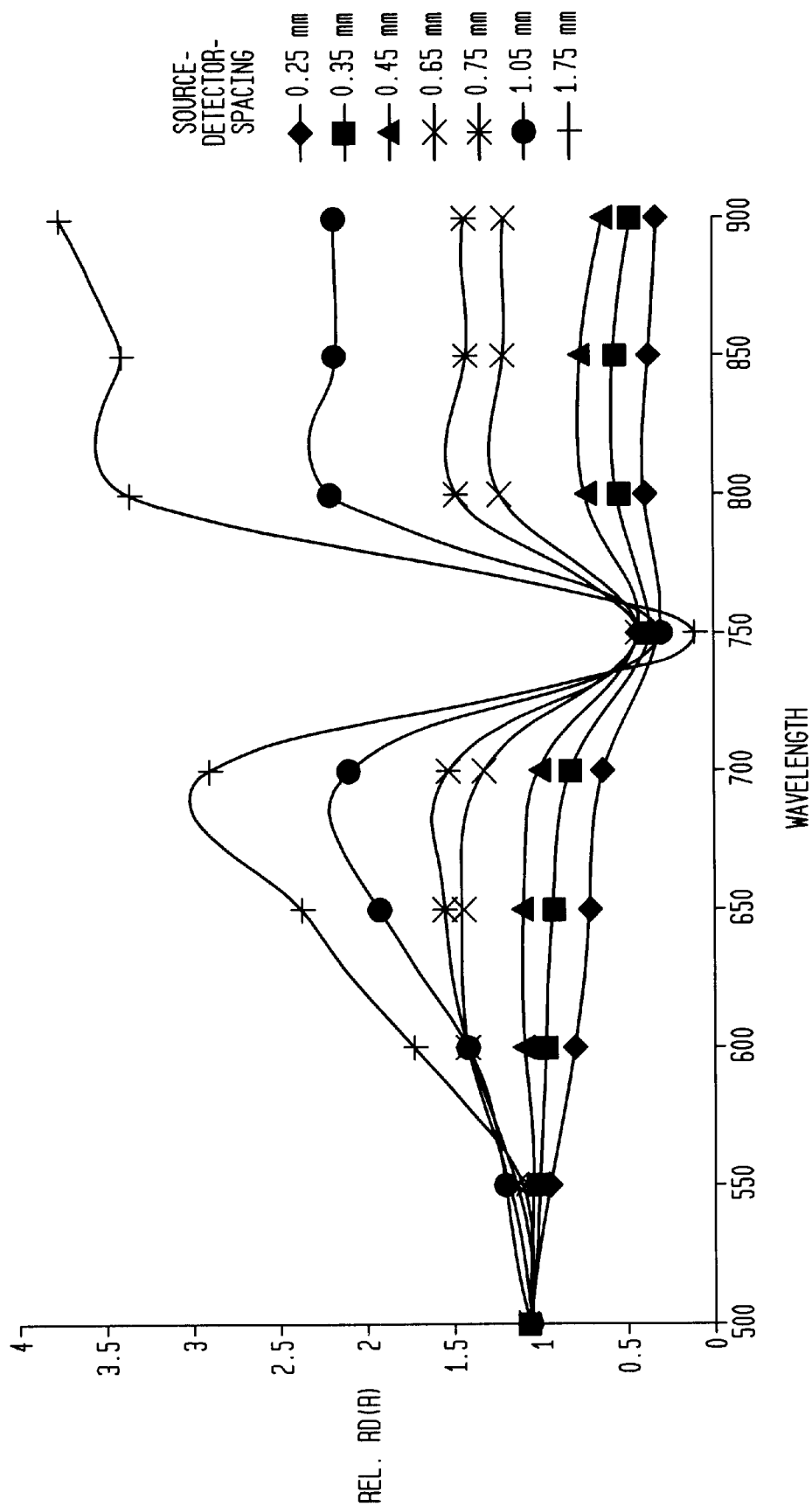
FIG. 2 is a graph of the relative photon output versus wavelength of Monte Carlo simulations for Intralipid and hemoglobin.

Particular features of the invention will be better understood from a consideration of the scale of absorption and scattering that occur in tissue, and the resulting effects on collected light that has interacted with tissue. Applicant has performed Monte Carlo simulations using absorption and scattering coefficients for a model system composed of intralipid (a scattering medium with scattering a coefficent similar to tissue) and hemoglobin (an absorbing material with an abosrption coefficient similar to blood), in concentrations or mixtures corresponding to various scattering and absorbing ranges of biological tissues. FIGS. 1 and 2 show the relative amount of reflected light plotted against wavelength λ for various source-detector spacings. In the plot of FIG. 1, where there is only scattering material, it can be seen that the amount of reflected light from a probe with a source-detector spacing between 0.65 mm and 0.75 mm is substantially independent of wavelength over the 500–900 nm band. In accordance with one aspect of the present invention, probes having this source-detector separation are constructed to minimize the effect of scattered light.

FIG. 2 illustrates the situation when both absorbers and scatterers are included in the Monte Carlo simulation. At a separation of 0.65 or 0.75 mm there is adequate resolution of the absorbance band from hemoglobin to measure the hemoglobin concentration without the influence of scattered light. The presence of static scatterers (as contrasted to, for example, a dynamically changing level of tissue scattering caused by onset of edema), simply introduces an offset of the received light amplitude, but does not alter or obscure the spectral shape. A processor/software system operating on the detected light spectrum may then simply subtract an offset corresponding to the strength of the scattered light signal present in the sample to obtain an absorbance spectrum from which a quantitative measure of the targeted analyte (e.g., hemoglobin, lactate or other material) is obtained. By setting a greater source-detector separation (e.g., 1.75 mm) the probe achieves a higher sensitivity to absorption and retains some sensitivity to scattered light. To study only scattered light with minimal contribution from absorbers present in the tissue, the source-detector spacing may be set at 0.25 mm. In practice, when determining a probe set-up for a particular tissue in accordance with the present invention, one specifies the probe absorption and scattering coefficients for the tissue of interest, then performs the Monte Carlo simulation to determine a suitable spacing.

In certain embodiments, discussed further below, the probe may include an element that adjusts the source-detector spacing to adapt the probe for different tissues, or for optimizing different assays (e.g., a scattering assay directed at cell or tissue structure, and a calorimetric assay directed at the presence or quantification of a particular analyte or condition) in the same tissue. In each case, the assayed tissue volume is below several cubic millimeters, and the optical path length followed in tissue by the photons collected by and detected at the detector may be on the order of one or several mean free path lengths.

Figure 3:
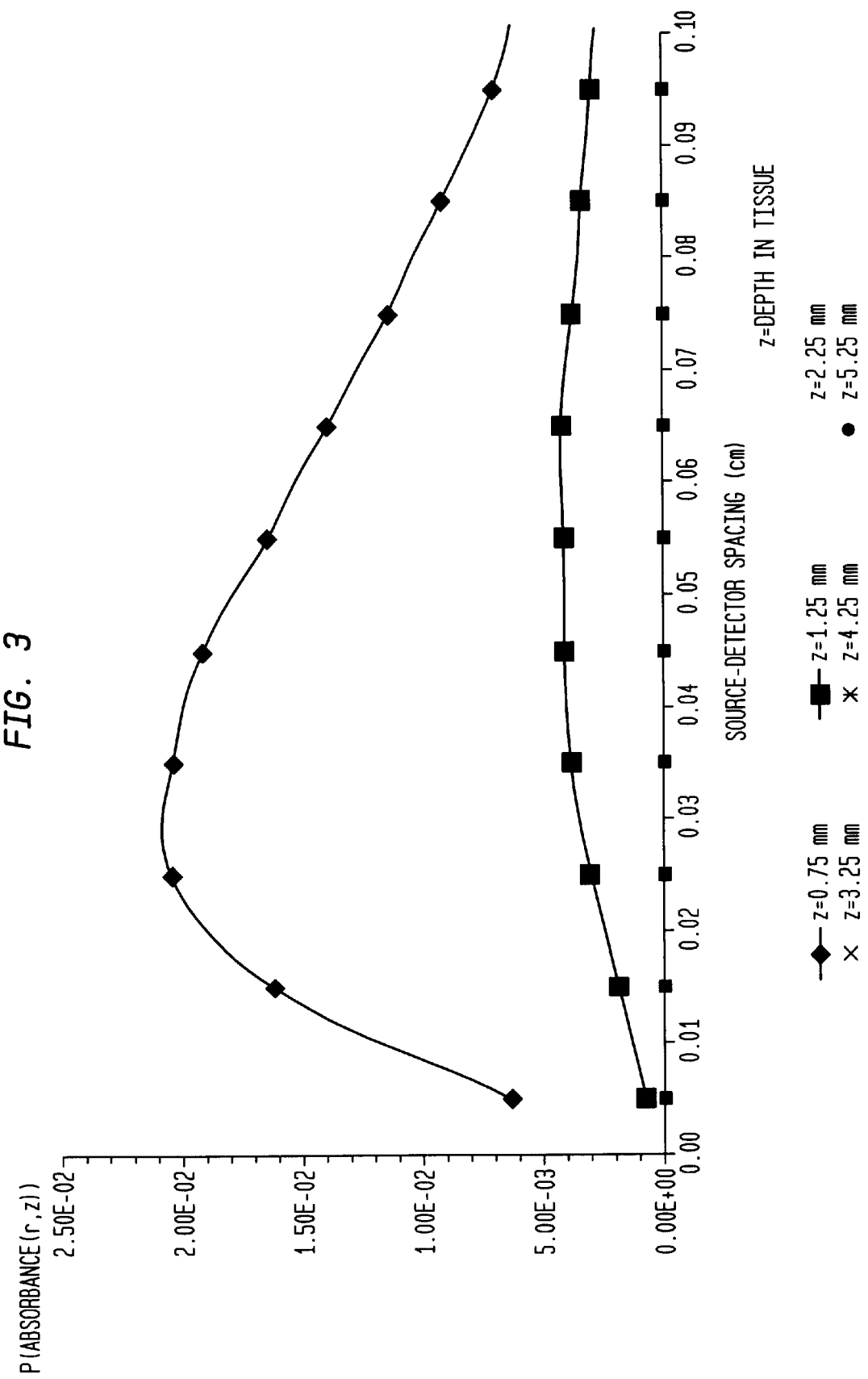
FIG. 3 is a graph of absorbance versus source-detector spacing for hemoglobin.

FIG. 3 illustrates another simulation, plotting the probability (P) that 750 nm light is absorbed at a particular point in a hemoglobin solution. At depths greater than 1.25 mm from the detector the number of remaining photons, and the probability of reflection back to the detector are very low; this implies that a meaningful absorption spectrum cannot be recorded. At depths less than 1.25 mm and source-detector spacing between 0.10 and 0.80 mm there is reasonable probability that light will be absorbed and the remaining light will be returned to the detector. Thus, this simulation shows that absorption spectra are essentially recorded from a narrow region of tissue close to the detector. Negligible signal is obtained at the absorbance peak for a source-detector spacing above several millimeters, precluding a quantitative spectral measurement. The present invention applies these simulations to provide effective spectrographic probes within the design constraint of a small-footprint probe, such as a fiber optic probe.

From these simulations it is seen for the model solution of tissue that source-detector spacing between 0.1 and 0.8 mm allow meaningful collection of absorption information and subsequent identification of a tissue component and/or calculation of chemical concentrations of species within the tissue. By choosing a specific spacing in that range, e.g., 0.65 mm to 0.75 mm, the wavelength dependence of scattering can-be minimized and adequate localization of the sample volume can be obtained, as discussed further below in connection with modeling results and representative spectrographic target compounds or tissue conditions.

Discussion of the Simulations

For these simulations, applicant performed Monte Carlo simulations with the ANSI Standard C code provided by Wang and Jacques, as available on the internet at the site (http://omlc.ogi.edu/software/mc/index.html). The modeling technique is discussed in various papers, notably Wang et al., "MCML—Monte Carlo modeling of photon transport in multi-layered tissues," Computer Methods and Programs in Biomedicine 47:131–146, 1995, and in Wang et al., "CONV—Convolution for responses to a finite diameter photon beam incident on multi-layered tissues," Computer Methods and Programs in Biomedicine 54:141–150, 1997. A cylindrically symmetric geometry was assumed with a point source at radius r=0. The relative index of refraction at the source was set equal to one, and the anisotropy factor, g, set to 0.9. This corresponds to the source being inside the media, (e.g., the probe is inserted into tissue), and simulates the typical anisotropic scattering properties of tissue. The number of incident photons, N, was set to 10,000. All output values are normalized by N to obtain probability.

In performing the Monte Carlo calculations, the radial resolution of the simulation was set to 0.1 mm, and the depth resolution was set to 0.5 mm. The grid was set to follow photons to a 30 mm radius and a 20 mm depth away from the source. Modeling was carried out for the wavelength region 500 to 900 nm, in 50 nm increments. Purely scattering models of Intralipid were performed using the measured scattering coefficients as a function of wavelength provided by van Staveren et al., "Light scattering in intralipid-10% in the wavelength range of 400–1100 nm," Applied Optics 30:4507–4514, 1991 (that publication is hereby incorporated by reference herein), and using absorption coefficients from Flock et al., "Optical properties of Intralipid: a phantom medium for light propagation studies," Lasers in Surgery and Medicine 12:510–519, 1992 (which is also hereby incorporated by reference). The values are valid for Intralipid-10% concentrations between about 4 and 17 volume percent; however, it will be understood that these optical properties of Intralipid are approximate, due to real variation in scatterer size and preparations. Intralipid also has some absorption at the longer wavelengths due to water, and its scattering properties are a function of wavelength.

To investigate possible source-detector separations that would reduce the wavelength dependence of scattering, the simulations were performed with the following approximate changes in absorption and scattering coefficients as a function of wavelength taken into account: the absorption ($\mu_a$)

and the scattering ($\mu_s$) coefficients input to the code were between $5.5 \times 10^{-5}$ to $0.06$ cm$^{-1}$ and about 206 to 846 cm$^{-1}$ respectively, based on wavelength. The standard deviation across wavelengths was used as a measure of the wavelength dependence of scattering for each radial distance. Absorption and scattering models were performed using absorption coefficients for a 2 mM deoxy-hemoglobin solution with the same scattering coefficients used above. Tabulated molar extinction coefficient values of hemoglobin (deoxygenated form) were converted to absorption coefficients by 2.303X (molar concentration). The values for the molar extinction coefficients in [cm–1/(moles/liter)] were compiled using data from W. B. Gratzer, Med. Res. Council Labs, Holly Hill, London, and N. Kollias, Wellman Laboratories, Harvard Medical School, Boston. The 2 mM concentration of hemoglobin corresponds to approximately 13 g/dl, which is a physiologically relevant level for blood. The absorption coefficients input to the code were between 3.5 and 246 cm$^{-1}$ for these models, with scattering coefficients as above. The effective depth that reflected photons return from is estimated by the probabilities of absorption as a function of radius and depth.

Monte Carlo Modeling Results

The relative photon output from the simulations for each set of $\mu_a(\lambda)$ and $\mu_s(\lambda)$ in Intralipid is shown in FIG. 1. The values are normalized to the photon output per cubic centimeter at 500 nm. The different reflectance profiles are shown for various distances away from the source. For source-detector separations between 0.45 and 0.75 mm, scattering as measured by the standard deviation from 500 nm, is minimized as illustrated in Table 1.

TABLE 1

Minimization of scattering-reduction of standard deviation from 500 nm

| Source-Detector Spacing (mm) | Standard Deviation |
| --- | --- |
| 0.25 | 0.235 |
| 0.35 | 0.199 |
| 0.45 | 0.133 |
| 0.65 | 0.114 |
| 0.75 | 0.139 |
| 1.05 | 0.331 |
| 1.75 | 0.641 |

The probability of absorption at each distance away from the source was computed from the photon output per area by multiplying out the grid geometry. Intralipid and hemoglobin simulations at 750 nm show that the total absorbed fraction of incident photons are 6.4% and 72.5% respectively. For Intralipid, 90% of the 6.4% total absorbance probability occurs when the depth is less than 1.2 cm. Further decomposition of the data into its radial (r) and depth (z) components shows that the probability of absorption increases, then decreases at a depth of 0.75 mm as the radial distance away from the source (corresponding to the source-detector spacing) increases.

Hemoglobin (deoxy form, $Fe^{2+}$) has a strong absorbance at 760 nm. The probability of absorption shown here at 750 nm is seen to be much higher than the purely scattering model. All of the absorption occurs by a depth of 3 mm, and 90% of the total absorption occurs by a depth of 0.75 mm. Similar trends occur for increasing source-detector spacing as in Intralipid when the data is decomposed into its radial and depth component. FIG. 3 shows a marked decrease in the absorption probability for all source-detector spacing after a depth of 1.25 mm.

Since optical fibers have a finite diameter on the order of the radial grid size (100 um core for example) and possess a numerical aperture, the real source is not a point source. The simulations shown here for a point source were therefore convolved for a finite Gaussian beam. The trends in the convolved simulations are similar to the point source simulations. The accuracy of the probability (per cm$^3$) is proportional to the square root of the number of incident photons, N. Larger values of N may improve the statistical error, but do not affect the trends, i.e., the photons will follow the same most likely paths for, a given set of optical properties. It was therefore assumed that trends observed in a cylindrically symmetric geometry could be applied to a linear source-detector separation configuration. The simulations provide useful trends for a two fiber sensor.

From these simulations, it is estimated that the tissue depth interrogated by a source detector separation of 0.75 mm is approximately 1.25 mm in an absorbing medium. For source-detector separations less than 0.75 mm, this depth is smaller as the probability of absorption increases. Since the propagation was modeled as forward directed (g=0.9), this depth may appropriately be taken as the most likely deepest layer of tissue from which photons could scatter back to the detector. For comparison, diffusion theory predicts a penetration depth (defined as $\delta = 1/(3\mu_a(\mu_a + \mu_s(1-g)))^{1/2}$) of 0.04 to 0.64 nm for the optical properties simulated here. The probability of absorption at a depth of 1.25 mm is approximately half of the probability at a depth of 0.75 mm, where 90% of the absorption occurred. The probability of photons visiting this layer and returning back to the detecting layer is reduced significantly. This limit corresponds to a spherical volume of about one cubic millimeter for a 0.75 mm source-detector spacing.

Probe Designs

Based on the foregoing considerations applicants have designed a number of probes for tissue spectroscopy.

The fiber optic sensors described here are simpler and should be less costly to fabricate than probes employing a chemistry-based tip sensor. They are also intended to be more rugged, with the incorporation of metal fibers, needles or other structural or reinforcing elements for placement and strength, permitting extended use in the tissue being studied or monitored. Small fibers from 50 to 200 um core sizes can be used along with proper source-fiber and detector-fiber spacing to optimize sensor performance.

Figure 4:
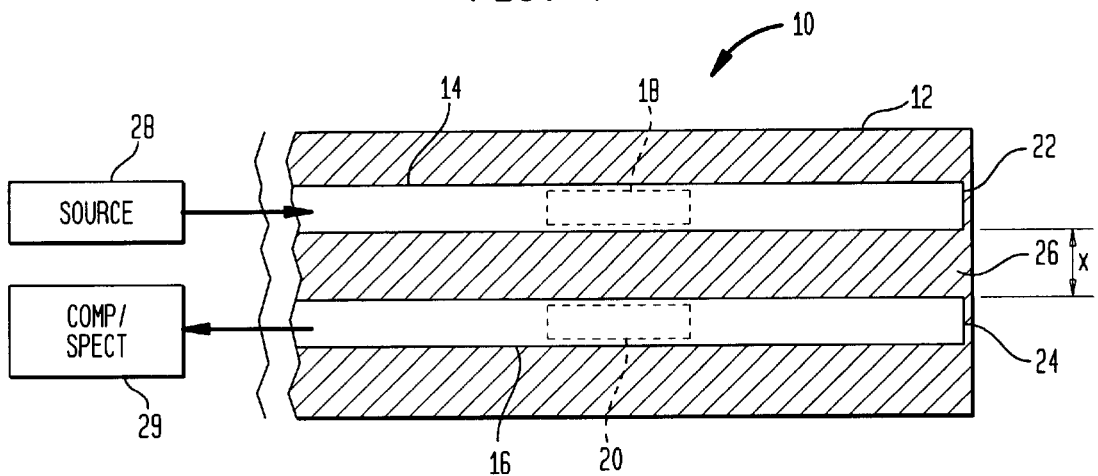
FIG. 4 is a cross-sectional side-view of a tissue probe according to the invention.

Referring to FIG. 4, one embodiment of a probe 10 is a side-sensing probe including a small section of stainless steel housing 12 supporting a source-fiber 14 and a detector-fiber 16. A section 18, 20 of the fiber cladding on both fibers is symmetrically removed from adjacent regions of the respective fibers to define the tissue illumination and detection windows, allowing light to pass through from source-fiber 14 into adjacent tissue and reflect back into the core of the detector-fiber 16. For this embodiment, total internal reflection may be maintained at the fiber distal ends 22, 24 by placing material 26 having the same index of refraction as the cladding at the fiber ends. Fibers may also be terminated by polishing and deposition of a reflective coating, or by other suitable preparation or construction.

The probe connects to a console or suitable unit which typically houses the spectral analyzing components and may also contain a light source. Light travels from the source 28, e.g., a broad band source (such as a tungsten lamp, a tungsten-halogen lamp, a xenon arc lamp, or a source with discrete light generators such as light emitting diodes, laser diodes, or lasers), through fiber 14, is reflected by the sample, and enters fiber 16. The collected light signal returned by the fiber 16 is processed by a computer/spectrometer 29, e.g., a spectrometer including a processor and a detecting element to measure the intensity at various wavelengths of the light signal received through the detector-fiber. The spectrometer can contain a dispersing element to separate the broadband light into specific wavelengths.

In the device of FIG. 4, the separation, X, of the fibers placed side to side, can be manipulated in fabrication by forming different spaced grooves in the housing to allow selective placement of the fibers at different separations, so that the probe may be initially set up, or re-configured, to probe different depths into the tissue, and optimize sensor performance for different tissues, or for different absorbances of targeted analytes.

The separation of the source-fiber and detector-fiber is determined by Monte Carlo modeling as described above for the specific application. In representative clinical applications, the probe can be inserted directly into tissue such as the myocardium, or may, for example be placed on a surface, such as the internal surface of the bowel or in a blood vessel to study the epithelium or to detect atherosclerotic plaque. The probe can also be placed on the surface of a tissue suspected to be cancerous.

Figure 5:
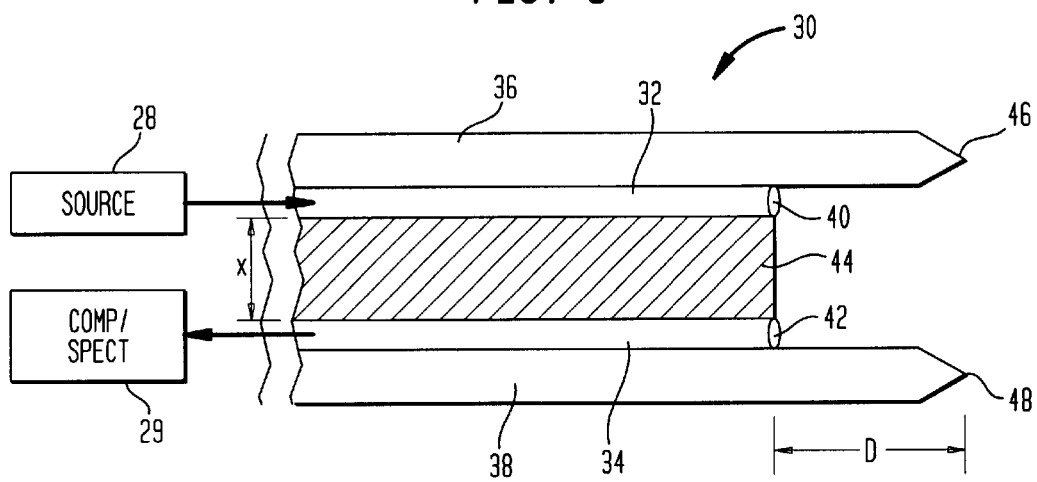
FIG. 5 is a side view of an alternative embodiment of a tissue probe.

Referring to FIG. 5, another embodiment is an end-sensing probe 30 that positions a source and a detector at the end of the assembly. As shown, this embodiment includes two fibers 32, 34 mounted to taper point needles 36, 38. Light exits source-fiber 32 through its distal end 40 and enters detector-fiber 34 through the distal end 42 of that fiber. A spacer material 44 is placed between the fibers, both to provide structural strength and to fix the source-detector spacing X, chosen for the application. The fibers are placed an optimal distance, D, from the needle points, 46, 48 to control the placement depth of the probe insertion in tissue. Light travels from source 28 through fiber 32 and is reflected by a sample tissue volume located between the positioning/insertion needles 36, 38. Light collected by the fiber 34 is processed by computer/spectrometer 29. Probe 30 is placed a known depth into the tissue. The probe 30 can be inserted directly into tissue such as the myocardium, a tumor, or an area suspected to be cancerous.

Figure 6B:
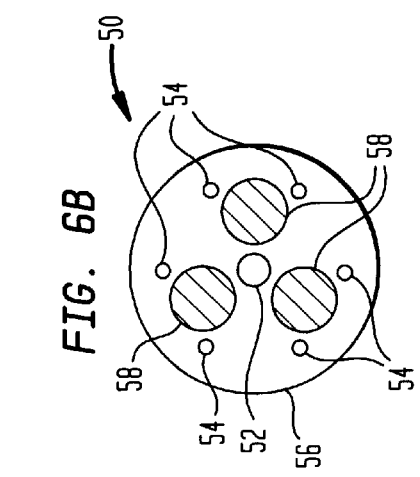
FIG. 6B is an end view of the tissue probe of FIG. 6A.
Figure 6A:
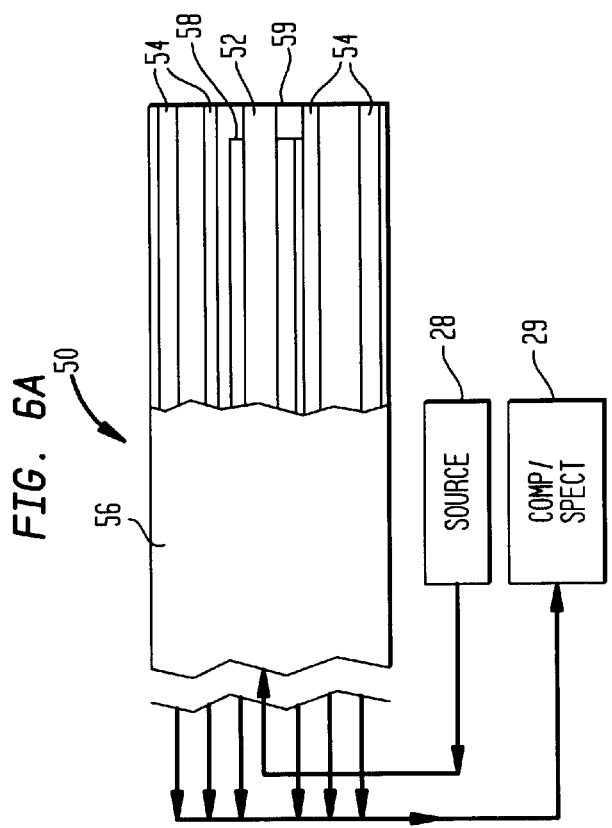
FIG. 6A is a cross-sectional side-view of an additional alternative embodiment of a tissue probe.

Referring now to FIGS. 6A and 6B, there is shown a partially cut-away view and an end view of another embodiment of a probe 50 according to the invention. Probe 50 includes a many-to-one detector/source arrangement to define both a small tissue volume and a desired spectral response sensitivity. In the illustrated embodiment, a suitably-sized source-fiber 52, such as a 200 micrometer fiber, is placed in the middle of a ring of plural, e.g., six, smaller detection fibers 54. Fibers 52, 54 are integrated in the configuration shown in a protective sheath 56 with several semi-flexible metal strands 58 located between the fibers. The strands 58 provide a stiffness that allows penetration into tissue without requiring a needle or use of a stylet structure; the strands also prevent excessive flexing of the probe, which might introduce strain in the fibers and degrade their transmission characteristics. Depth markers can be placed directly on the metal strands or on a surrounding protective sheath to guide a surgeon when inserting the probe. Alternatively, rather than metal strand reinforcements, the fibers may reside in a gel within the sheath, wherein the gel is selected to have a sufficient modulus to stiffen the assembly while still being somewhat compliant, preventing excessive strain in, or breakage of, the fibers. The fiber spacing may be stably maintained by the metal strands 58 and sheath 56. In this embodiment, light travels from the source 28 through fiber 52, is reflected by a sample located directly under the end 59 of the probe, and is collected by the six smaller detection fibers. Light collected by the six detector fibers 54 is processed by computer/spectrometer 29.

Figure 7:
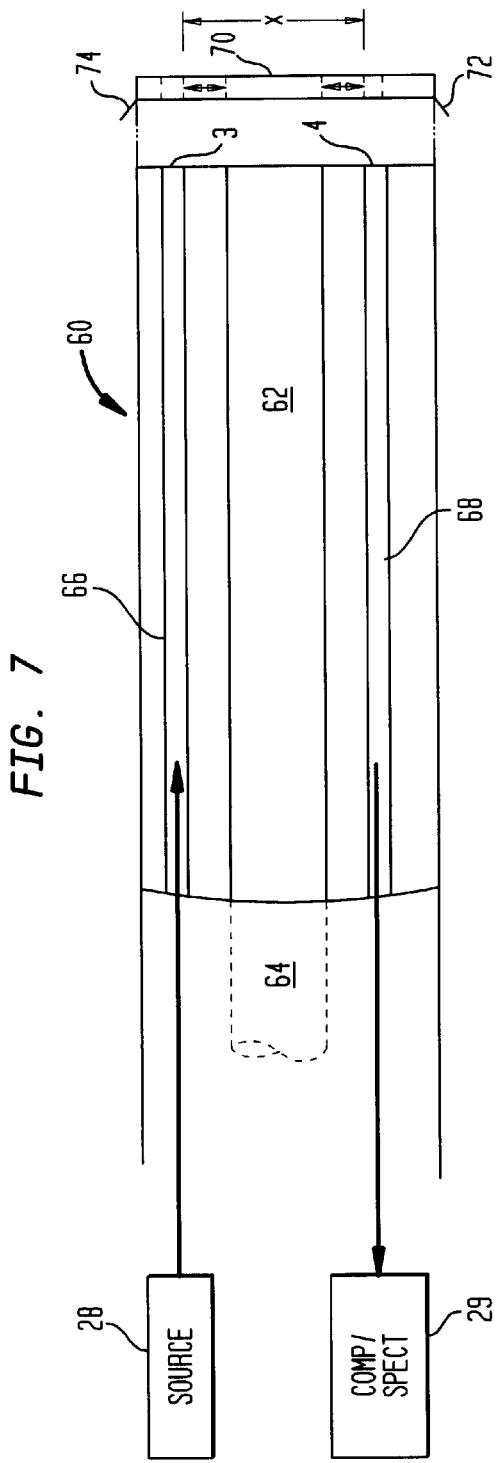
FIG. 7 is a side view of an additional alternative embodiment of a tissue probe.

FIG. 7 illustrates another embodiment 60 of a probe in accordance with the present invention. Probe 60 includes a central spacer tubing 62 that is connected to an introducer 64. A needle or stylet (not shown) can be passed into introducer 64 and through the spacer tubing 62 to effect penetration into the tissue. The source fiber 66 and the detector fiber 68 are loosely placed to run along either side of tubing 62 to a face plate 70. The face plate 70 is configured to maintain or to adjust, e.g., to increase or decrease, the spacing, X between fibers 66, 68 by moving the fiber ends radially closer or further apart. The faceplate 70 can also include barbs 72, 74 for securing the tip in place in the tissue. Depth markers can be placed on the stylet. After the stylet is removed, light travels from source 28 through fiber 66 and is reflected by the sample directly under the end of the probe. Light collected by fiber 68 is processed by a computer/spectrometer 29.

Each of the illustrated embodiments will be understood to have a generally elongated probe body that may, for example in the case of a catheter-like embodiment be similar in construction in many respects to many interventional or diagnostic catheters. Each fiber may have a suitable connector at its proximal end for connection to the source or spectrographic processor, and may pass through or connect with a hand piece having a stylet introductuion port, light ports or other similar features appropriate to mode of insertion or use.

As discussed above, each of these probe designs may be implemented, by setting the size and spacing of the source-detector portions, to interrogate a small tissue volume with a particular sensitivity to absorbance or both absorbance or scattering; the Monte Carlo modeling for the characteristic dimensions chosen allows the collected light signal to be processed for quantitative analyte assays, as well as meaningful determinations of structural characteristics. The sampled tissue volume may be as small as 0.015 $mm^3$ or as large as 2 $mm^3$ or even 5 $mm^3$, and the light source provides broad band illumination, or plural discrete wavelengths in a wavelength band of 400 to 2500 nm.

When the probe is to measure the concentration of a particular analyte present in the tissue (e.g., by applying Beer's law or suitable spectral processing), the spacings are preferably set to maximize sensitivity to absorption coefficient and to minimize sensitivity to, or dependence on, scattering. Sensors of this construction may be employed for assays such as measuring the level of lactate in muscle or organ tissue, or measuring the concentration of an exogenous tracer dye that has been placed in the bloodstream and accumulated in tissue for disease diagnosis. The probe may also be employed to measure the level of lactate, pH or a chemical constituent in an extremely heterogeneous matrix, such as in atherosclerotic plaque, in a tumor, or in a wound where it is desired to minimize the contribution of light scattered by physical structures.

Advantageously, the step of applying Monte Carlo modeling to simulate the interaction of light with tissue over a path of small dimension allows well-quantified spectral measurements to be obtained from small tissue volumes. These tissue volumes may be comparable to small volumes probed by some existing techniques, such as microelectrode based techniques, but may also be appreciably smaller than the volumes achievable with existing probes of other types. For example, a microelectrode of 0.75 mm diameter that displaces approximately two cubic millimeters and probes a tissue surface area of about 1.8 square millimeters, may be replaced by a probe of the present invention having a source-detector separation of 0.5 millimeters. In this case, calibration equivalence is readily established using a comparable-volume microelectrode reference. Similarly, a 1.6 millimeter esophageal electrode (with 8 mm$^2$ surface area and 2 mm$^3$ displacement volume) as used for cardiac tissue monitoring may be readily correlated to, and functionally replaced by, a probe of the present invention having a source-detector separation of 0.75 mm. Smaller source-detector separations are physically feasible using currently available optical fibers, with separations between 0.05 mm and 0.5 mm to achieve submillimeter tissue volume resolution and effective depth penetrations under 0.25 to 0.75 millimeters.

The described fiber optic probes can advantageously be applied to measure tissue pH and oxygenation in tissues such as the heart, muscle, bowel or liver. In the case of cardiac monitoring, the probe may be configured to monitor myocardial condition and provide protection during open or minimally invasive heart surgery. The elongated tubular construction allows these small probes to be left in the patient's chest post-operatively, and to be simply removed in the ICU in a manner similar to how a pacing wire is removed. When applied to muscle, bowel or liver tissue, the probe may monitor muscle, bowel or liver pH and oxygenation, to provide an early indicator of shock and allow appropriate interventions to be quickly initiated. Such monitoring can be used to guide resuscitation therapy. Used as a bowel probe, the unit can be placed through a feeding tube or endoscopically. Similarly, as a liver probe, the unit can be placed endoscopically to provide timely and sensitive assays during a liver transplant. The muscle probe would be placed directly in a peripheral muscle, such as in the arm or leg. The probes, particularly the muscle probe, can also be used to monitor shock in intensive care unit patients. Several small probes may be used together to simultaneously monitor different tissue sites in a wide area of tissue (such as arm or leg muscle) that may have differing levels of blood flow.

The same probes can be used with a number of different spectral analysis methods to probe local areas of tissue, such as optical methods for diagnosing cancer (e.g., applying correlation with a library of tissue spectra, or applying multivariate analysis to identify presence or concentration of a target material). The spatial localization of the probe volume also provides enhanced signal levels of interest for identifying foci of particular tissue conditions such as vulnerable formations of plaque in atherosclerotic arteries. In these methods, an absorbance spectrum is taken and one or more algorithms, such as a partial least-squares regression, are used to identify chemical compositions, classify tissue by spectral and/or scattering properties, or derive a measure of analyte concentrations. The probes allow the user to analyze a known region of tissue and improve the performance of the algorithms and the accuracy of measures by limiting the wavelength or amplitude dependence otherwise introduced in a collected signal by unwanted scattered light.

Probes of the invention are also advantageous for quantitative or qualitative analysis of chemical species in a heterogeneous matrix, applying multivariate calibration techniques to derive further results where light scattering from physical structures of the probed tissue adds information to the analysis. Such applications for sensors of the invention may include applications to pH measurement in organs (muscle, liver, bowel, heart, lung) where light scattering from cell size may be correlated with tissue pH change. Another such area is the classification of plaque types, where some structures, like calcified areas, present in the affected tissue will scatter, rather than absorb light. Similarly, the probes may be used for classification of tumors in various tissue beds, wherein the affected tissue may include localized areas of ischemia and hard tissue. In such cases, the volume or depth of the probed tissue may be set (by selection of a side- or end-source/detector spacing arrangement and fiber size as discussed above) to effectively resolve the pathological regions while detecting the scattering and/or absorbance features of interest.

In these applications, the method of the present invention readily produces a fiber optic probe having a millimeter-range probed tissue volume and source/detector separations that achieve a spectrally-flat or wavelength-independent scattering component over a range that allows the probe to readily detect and quantify absorbance peaks of a targeted material in the subject tissue region. For example a separation in the range of 1.0 to 1.75 mm may be used to probe such a volume up to an effective tissue depth of 1.25 mm for the 750 nm absorbance peak of deoxy-hemoglobin, providing a useful indicator of stress, metabolic state, shock, ischemia or a correlated condition in many tissues as discussed above. In general, by Monte Carlo modeling the scattering and absorbance of a particular tissue and a targeted material, applicant is able to set a source detector spacing that achieves the signal that accurately reflects the targeted material of interest (e.g., without skewing by excessive scattered light, or return components in which the absorbance band of interest had been depleted), so that the optics are matched to the intended assay.

It should be noted that while FIGS. 4–7 illustrate elongated probe embodiments especially suited for transcutaneous or endoscopic use, the source and detector elements need not be coupled by optical fibers to the targeted tissue. In other embodiments of the invention, small illumination elements (such as LEDs or laser diodes) and detection elements may be mounted in the probe body to directly contact the targeted tissue, for example to contact a tumor, a wound, or an exposed muscle. The source/detector spacing may also be set to contact the skin and probe a tissue volume (e.g., muscle) below the skin. Such probes may have a rigid body or shaft, or may have a physical form similar to the flexible catheter-type embodiments of FIGS. 4–7, or may take the form of a flexible sheet conformable to the tissue surface. Hybrid embodiments are also possible, e.g., with direct-contact LEDs for illumination, and fibers positioned for detection, or with the light-generation and detection elements mounted within a catheter tip, but coupled by short fibers to appropriately-spaced tissue windows.

In addition to the foregoing refinements and extensions of tissue measurement and in vivo spectroscopy, embodiments of the invention may also be applied to create a novel imaging system, wherein a plurality of source/detector sets, or fiber pairs are assembled together in an assembly or bundle to form the probe, such that each set interrogates one small tissue region. Each tissue region constitutes a "pixel", i.e., a matrix position of a larger region at which the bundle is directed. In this embodiment, the return signal from each pair may be processed as described above (e.g., to detect an absorbance and quantify the concentration of a compound, and/or to detect a scattering characteristic). The return signals of different pairs may also be processed or compared to detect other pathological conditions of interest for particular tissues, such as to create a map of the varying concentration of a detected compound in the imaged region, to form a map or survey of a region for small isolated distribution of spectral signatures of growing tumor material, or to identify a structural or histopathological condition such as clumping, striation or graininess, or other feature. In the latter cases, such "image analysis" processing may be implemented in particular embodiments with simplified threshholding, summing or other processing to quickly detect the sought-for pathology, pattern or distribution. The multiple source/detector fiber pairs may be placed quite closely, and may be separately multiplexed ON and OFF to prevent crosstalk or corruption of spectra from adjacent regions, producing point-like matrix spectral samples for survey, dimensional or structural determinations of a cell bed contacted by the probe.

Figure 8:
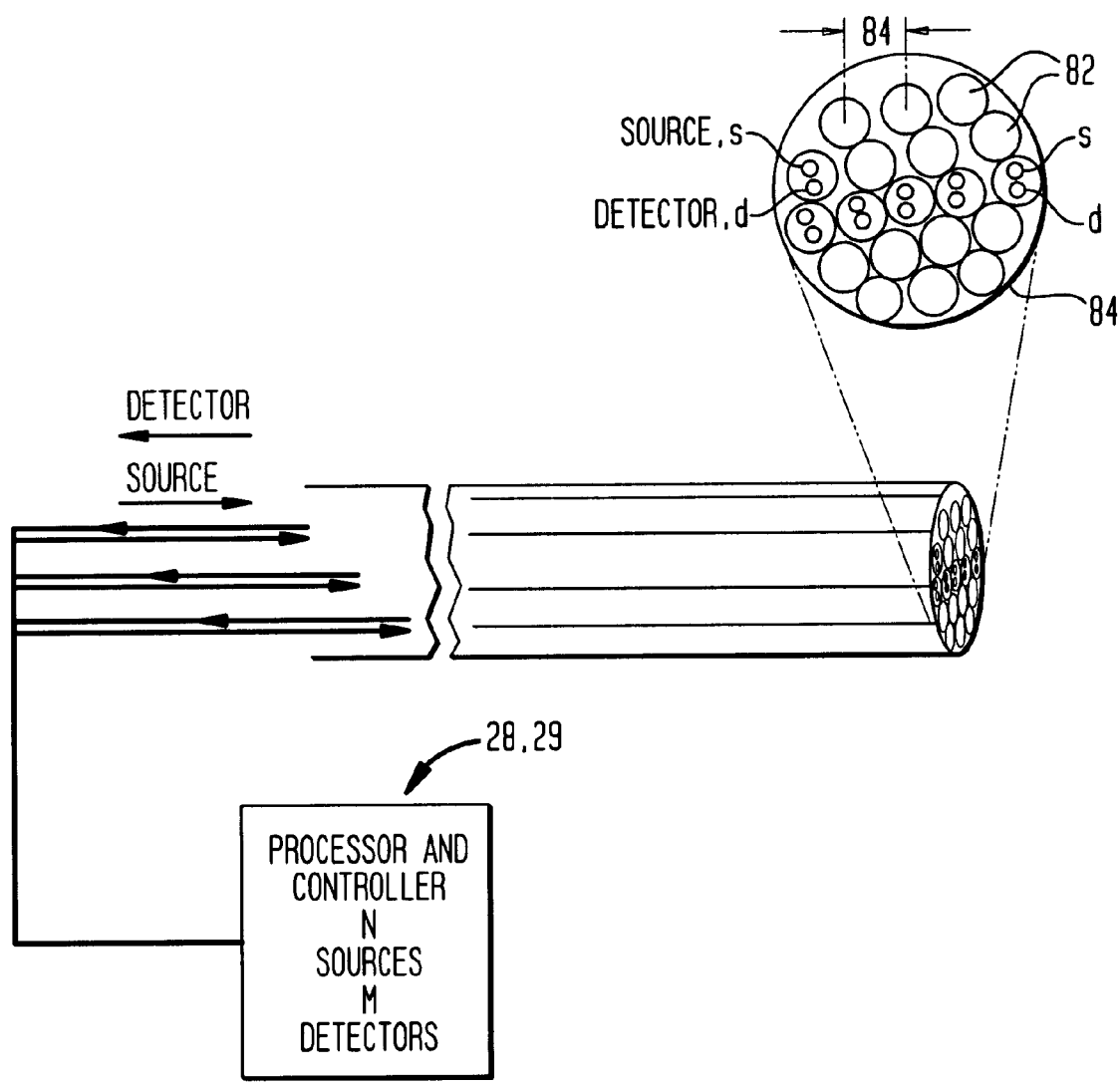
FIG. 8 shows an embodiment with multiple source-detector sets for survey or imaging.
Figure 8A:
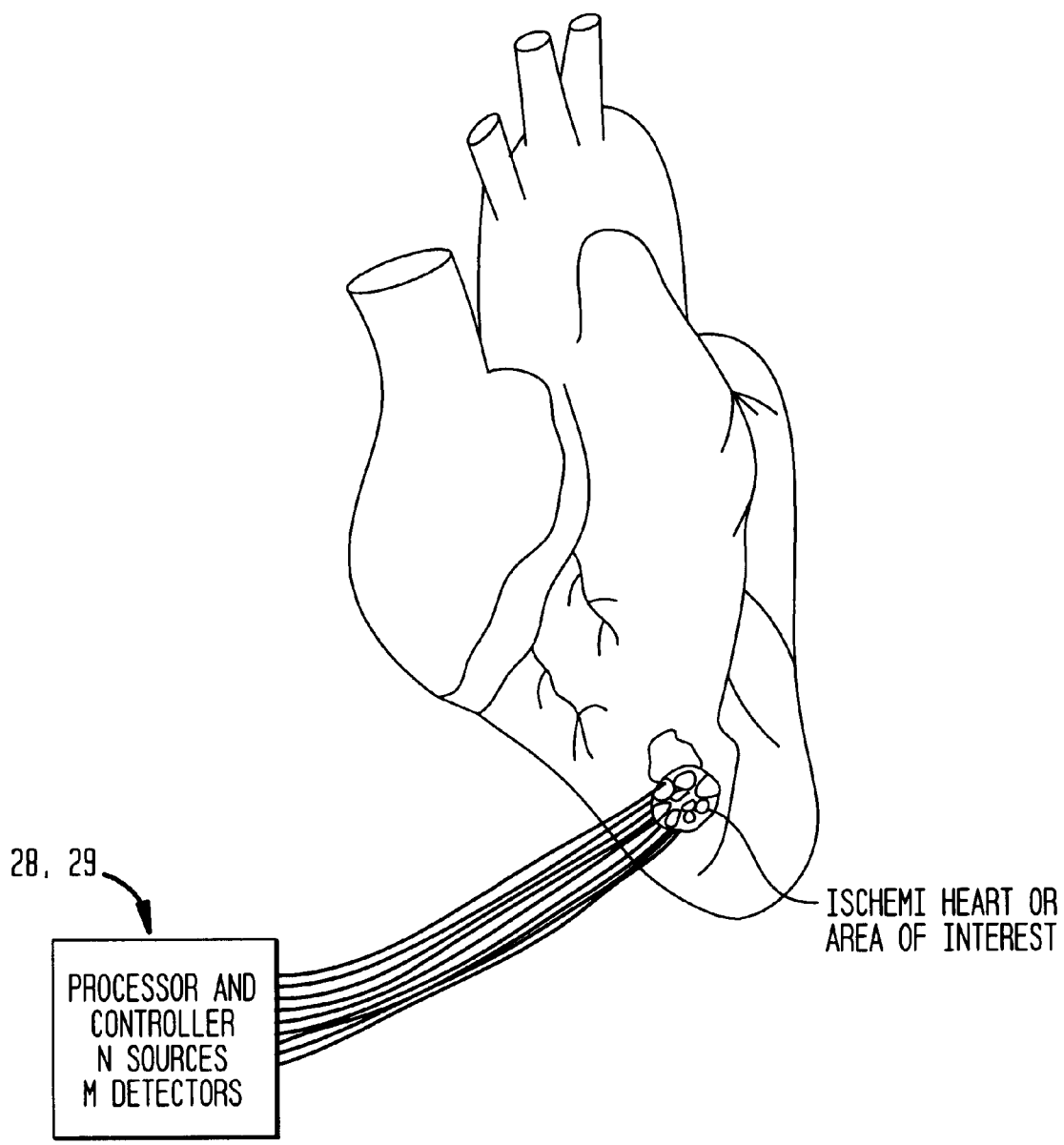
FIG. 8A illustrates the probe of FIG. 8 applied to detect ischemic tissue in a cardiac region of interest.

FIG. 8 schematically illustrates such a probe 80 having a plurality of source-detector sets 82 or pixel-probes, of which only nineteen are illustrated, arrayed at a spacing 84 on a tissue-contacting end face thereof. The spacing 84 approximates a desired spatial resolution, while each single set 82 may include one or more source-fibers and one or more detector fibers, configured to define a small and controlled interaction volume like any of the individual probes 30, 50, 60 discussed above. A corresponding multi-set probe may also be constructed using side-directed fibers as describe for the probe embodiment of FIG. 4 above. In use, as shown in FIG. 8A, the probe may be placed in contact with tissue to perform spectrographic measurements over a region of tissue. FIG. 8A illustrates placement directly on the heart, e.g., during open surgery, to monitor for or detect the limits of ischemia in a region of interest.

In the array or bundle probe 80 of FIG. 8, the source-detector spacings of different ones of the pixel-probes 82 may all be the same, and the probes 82 may form a relatively dense array, such as a packed bundle, or an n×m rectilinear array so as to produce multiple spaced point results from the tissue region. Alternatively, they may have different source-detector spacings and thus be configured to probe different depths or identify different spectral characteristics. As shown in the Figure, the fibers from the probe may connect to a processor/controller 28, 29 that activates or processes signals from the N sources and M detectors. Advantageously, in some embodiments the separation 84 may be set larger than the source-detector spacings such that all pixel probes 82 may be ON simultaneously without interference. Alternatively, the Processor/Controller may switch or multiplex the different sources and detectors (e.g., using micromechanical mirror arrays or solid state optical switching elements) to operate individual Ones sequentially, or to operate sets of widely-spaced non-interfering ones simultaneously, so as to acquire spectral determinations from all probes 82 of the bundle 80. The point or small-volume spectra so obtained may be convolved by the processor to provide a map of concentration of one or more constituents, to provide a structural determination over the region of tissue, or to assay a pathophysiological condition present in the region. Like the other embodiments described above, these multi-set "imaging" or "region-probing" probes may also be implemented using discrete electronics (small or nanotechnology lights and detectors) rather than fibers to directly contact or probe tissue volumes at the selected source-detector spacing. In that case, the elements may be mounted on a flexible support sheet, or on a small rigid movable contact head that may be placed against tissue. The imaging probes may also be implemented using a hybrid combination of direct contact elements and fiber-coupled elements to define the selected source and detector spacing in tissue. In that case, some or all of the connections to the processor/controller may be electrical leads rather than optical fibers.

Probes of the invention can be placed surgically, delivered endoscopically or through a catheter into a blood vessel or into tissue, or they may also be placed directly on the skin or on structures on the surface of the skin, such as wounds, lesions or tumors. While the probes of the invention have been described above with respect to several different embodiments to illustrate basic implementations of fiber-based illumination and detection configurations, and mounting structure, it will be appreciated that the method of implementing a small-volume probe for spectral collection of tissue signals may take other forms, may employ diverse light-generating and light detecting elements or arrays of elements that either directly contact tissue or are coupled thereto by fibers, and may be applied to assays and detection of materials and pathologies other than the specific examples described herein.

The invention being thus described, variations and modifications will occur to those skilled in the art, and all such variations and modifications are considered to be within the scope of the invention, as described herein and encompassed within the claims appended hereto and equivalents thereof. Other embodiments are within the scope of the following claims.

What is claimed is:

1. A side-sensing fiber optic probe for interrogating tissue, comprising:
   a probe body including a housing configured for holding fiber optics in a side-to-side arrangement,
   a first fiber optic enclosed within the housing for delivering light to a region of tissue, and
   a second fiber optic enclosed within the housing and held apart by a predetermined spacing from the first fiber optic for receiving light from the region of tissue, the predetermined spacing being based on Monte Carlo simulations to optimize a collected signal for a desired tissue sample,
   wherein the housing includes a tissue illumination window for exposing a portion of the first fiber optic, and a detection window for exposing a portion of the second fiber optic, the windows being positioned on a side of the housing so as to allow light to pass through the illumination window from the first fiber optic into the region of tissue and reflect back into the detection window to the second fiber optic when the probe is placed against the tissue.

2. The fiber optic probe of claim 1, wherein the spacing is set to achieve a desired sensitivity to scattering and absorbance.

3. The fiber optic probe of claim 1, wherein the fiber optics are held within grooves in the housing, and the housing contains different spaced grooves to allow selective placement of the first and second fiber optics at different separations to optimize a collected light signal for a given material or tissue.

4. The fiber optic probe of claim 1, wherein the spacing is set within a probe volume corresponding to size of a tissue feature or region of interest.

5. The fiber optic probe of claim 1, configured for penetration of tissue.

6. The fiber optic probe of claim 1, wherein the spacing is set to probe a tissue volume under several cubic millimeters.

7. The fiber optic probe of claim 6, wherein the spacing is set to probe a tissue volume under about one cubic millimeter.

8. The fiber optic probe of claim 7, wherein the spacing is set to probe a tissue volume under about 0.25 cubic millimeters.

9. The fiber optic probe of claim 6, wherein the probe is configured to spectrographically identify and/or measure concentration of one or more materials selected from among a dye, a treatment compound, and a tissue constituent.

10. The fiber optic probe of claim 6, wherein the probe is configured to spectrographically image a region of tissue.

11. The fiber optic probe of claim 1, wherein the windows are symmetrically positioned with respect to a longitudinal axis of the housing.

12. The fiber optic probe of claim 1, configured for direct insertion into a blood vessel to interrogate an internal surface of the vessel wall.

13. A method of analyzing a target tissue by detection of a spectrographic signal of interest, such method comprising the steps of:

placing a probe having a source and a detector in contact with the target tissue, wherein the probe includes a housing for holding apart the source and detector therein, the housing further including an illumination window for exposing a portion of the source and a detection window for exposing a portion of the detector, the windows being positioned on a side of the housing;

setting a spacing between the source and detector for selectively interrogating a limited volume of the target tissue;

illuminating the target tissue with light emitted from the source through the illumination window; and detecting light through the detection window with the detector, whereby the detected light provides information about the limited volume of target tissue, wherein the step of setting the spacing includes selecting the spacing based on a non-diffusion modeled interaction to probe a volume localized so as to preferentially detect the signal of interest.

14. The method of claim 13, wherein the probe has plural sets of sources and detectors, each set being positioned to image one of multiple localized volumes in the target tissue for forming a spectrographic image.

15. The method of claim 13, wherein the spectrographic image forms a map of concentration, state or tissue condition.

16. The method of claim 13, wherein the source and detector comprise optical fibers.

17. The method of claim 13, wherein the localized volume corresponds to absorbance depth of a target material.

18. A spectrographic probe for interrogating tissue to detect a signal of interest for spectrographic characterization, the probe comprising:

a probe body including a housing configured for holding an illumination source and a light detector mounted therein, the housing further having an illumination window for exposing a portion of the illumination source and a detection window for exposing a portion of the detector, the windows being positioned on a side of the housing, the illumination source being positioned by the probe body for delivering light through the illumination window to a region of tissue, the detector being positioned by the probe body a predetermined spacing from the source for receiving light through the detection window from the region of tissue, wherein the predetermined spacing is a small spacing effective to limit light received by the detector to light from a tissue depth that preferentially contains the signal of interest, thereby enhancing accuracy of the spectrographic determination.

19. The spectrographic probe of claim 18, wherein the predetermined spacing is set based on Monte Carlo modeling of tissue scattering and an absorbance.

20. The spectrographic probe of claim 18, wherein the source and the detector are optical fibers.

21. The spectrographic probe of claim 18, configured to penetrate tissue.

22. The spectrographic probe of claim 18, configured to contact a tissue surface.

23. The spectrographic probe of claim 22, configured to contact skin and illuminate a volume of target tissue lying below the skin.

24. The spectrographic probe of claim 18, configured for direct insertion into a blood vessel to interrogate an internal surface of the vessel wall.

* * * * *